United States Patent [19]

Walter et al.

[11] Patent Number: 4,597,762
[45] Date of Patent: Jul. 1, 1986

[54] COLLAGEN PREPARATION

[75] Inventors: Peter Walter, Unterpfaffenhofen-Harthaus; Michael Walter, Munich, both of Fed. Rep. of Germany

[73] Assignee: HEYL Chemisch-pharmazeutische Fabrik GmbH & Co KG, Fed. Rep. of Germany

[21] Appl. No.: 319,882

[22] Filed: Nov. 10, 1981

[30] Foreign Application Priority Data

Nov. 13, 1980 [DE] Fed. Rep. of Germany ....... 3042860

[51] Int. Cl.$^4$ .................. A61F 2/06; A61F 00/00; C07K 15/20
[52] U.S. Cl. ............................................ 623/1; 623/8; 623/12; 623/13; 623/15; 435/68; 435/69; 435/273
[58] Field of Search ............ 435/273, 68, 69, 272; 260/123.7; 623/8, 12, 13, 15, 1

[56] References Cited

U.S. PATENT DOCUMENTS

| 3,093,439 | 6/1963 | Bothwell | 260/123.7 |
|---|---|---|---|
| 3,131,130 | 4/1964 | Oneson | 435/273 |
| 3,455,776 | 7/1969 | Gister et al. | |
| 3,927,422 | 12/1975 | Sawyer | 128/334 R |
| 4,082,507 | 4/1978 | Sawyer | 128/1 R |
| 4,193,813 | 3/1980 | Chvapil | 260/123.7 |
| 4,223,984 | 9/1980 | Miyata et al. | 260/123.7 |
| 4,233,360 | 11/1980 | Luck et al. | 106/155 |
| 4,291,013 | 9/1981 | Wahlig et al. | 424/95 |
| 4,409,332 | 10/1983 | Jefferies et al. | 435/188 |

OTHER PUBLICATIONS

Webster's New World Dictionary (1973) 2nd ed. Simon and Schuster, p. 1472.
Brockhaus Enzyklopadie (1973) Brockhaus Wiesbades, p. 598.
Encylopaedia Britannica vol. 6 (Colebrooke to Damascuis) William Benton, publisher, pp. 272–274.
Methods in Enzymology (1982) vol. 82 Academic Press, pp. 3–7, 18–21 and 126–129.
American Dyestuff Reporter vol. 30, No. 17, Aug. 18, 1941, pp. 425–448.

Primary Examiner—Sam Rosen
Assistant Examiner—William J. Herald
Attorney, Agent, or Firm—Bierman, Peroff & Muserlian

[57] ABSTRACT

A collagen preparation comprising collagen-I for human or veterinary medicine obtainable by proteolyzing, cross-linking, reducing, optionally heat treating, and finally sterilizing mammalian collagen I material under conservation of its biological texture.

21 Claims, No Drawings

COLLAGEN PREPARATION

DESCRIPTION OF THE INVENTION

The invention relates to collagen preparations, a process for their production and their use in the human and veterinary science.

BACKGROUND ART

It is known that skin lesions occur frequently after burnings and accidental injuries. For their care autologous skin preparations have been used besides the usual treatment of wounds. The use of autologous skin preparations is, however, limited by the size of the defect. Therefore many attempts have been undertaken to use collagen forming a principal constituent of corium, fibrous tissue, tendines, fasciae, and ligaments in the field of medicine for instance as temporary skin graft, vascular graft (angioplasty) and so on (cf. for instance Umschau 66, 1966, 230). Concerning the attempts up to now to develop a suitable material for skin grafts it is referred to the monograph "Experimental Skin Grafts and Transplantation Immunity" by D. L. Ballantyne and J. M. Converse, Springer Verlag Berlin, 1979. Modified blood vessels from bovine (so-called bovine-heterograft) have been used for some years for blood vascular grafts (compare for instance Rosenberg, Surg. Forum 7, 1956, 243). These grafts did not fulfill the expectations since irreversible changes of the walls are caused by the penetration of substances from the blood running through. Therefore they are hardly used anymore nowadays.

Nothing is known about the production and the use of collegen preparations, their biological texture being preserved, for other medical applications. The use up to now of collagen preparations in the field of medicine is limited to spongy collagen. The biological texture of the collagen is destroyed in these cases causing changes of its physical and also of some biological properties (cf. for instance M. Chvapvil, Collagen Sponge, Theory and Practice of Medical Applications, J. Biomed. Mater. Res., 11, 1977, 721–741).

DISCLOSURE OF THE INVENTION

It is an object of the present invention to provide modified collagen preparations of animal origin for the human and veterinary therapy which can be stored for longer periods of time and can be transplanted or implanted immediately and in which the desired biological properties (for instance germ resistance, stimulation of the production of principal substances of cells, incarnant development of the granulation, haemostase and so on) of the natural starting materials have been preserved and the shape and physical properties thereof have been adapted to the corresponding use.

Therefore the present invention provides collagen preparations comprising collagen-I for human or veterinary therapy which are obtainable by the following consecutive steps:
(a) proteolyzing mammalian collagen I material,
(b) cross-linking the material obtained according to step (a),
(c) reducing the material obtained according to step (b)
(d) and finally sterilizing the material,
wherein, if desired, the material obtained according to step (c) is heated, optionally molded and "welded" if pieces of said material are to be connected and wherein the biological texture of the collagen-I material is preserved throughout all steps.

Skin, corium, fasciae, filament-like formations out of tendines, duct-like formations out of blood vessels and tubular hollow organs, bag-like formations out of pericardia and interstitial mammalian tissue are used as mammalian collagen-I material.

The starting material mentioned above is taken from mammals, preferably ruminants, especially from the goat, bovine and fetuses from bovine.

The proteolysis is performed in the presence of ficin and L-cystein in an aqueous medium at a pH from 5.5 to 6.5 and at a temperature from 30° to 50° C.; cross-linking is performed with 1 or more aliphatic dialdehydes with 2 to 10, especially 4 to 7 carbon atoms, preferably with 1–10% b.w. aqueous glutaric dialdehyde solution; the reduction is performed with alkali metal borohydride, especially sodium borohydride, in an aqueous medium and the heat treatment is performed with hot air saturated with steam at 80° to 100° C. for some minutes and in order to perform the process of molding or the "welding" of pieces of preparations the preparation or the pieces of preparations being closely to each other with their edges are pulled onto an inert, solid body having the desired shape and a smooth surface and there the treatment with hot air is continued.

When starting from thick collagen material it is first subjected to a primary proteolysis. Then it is given the desired thickness by cleaving it in the direction of the fibers. The material thus obtained is proteolyzed again and treated as described above.

Preferably after the proteolysis a treatment with a diluted aqueous sodium chlorite solution is performed in between.

The washing between the different process steps is performed with running water and lasts generally 24 hours each.

Preferably one treats the mammalian collagen I material for 8 to 24 hours with an aqueous solution containing 10 g of ficin/liter and 1 g of L-cysteine/liter at a pH of 6 and at a temperature of 37° C., treats then for 24 hours with a 1% aqueous sodium chlorite solution, waters, treats for 7 days with a 1 to 10% aqueous glutaric aldehyde solution, washing with water, treats for 24 hours with an aqueous sodium borohydride solution, washing with water and sterilizes finally whereby the washing is performed with running water and lasts for 24 hours each.

In order to obtain collagen preparations consisting out of tubular hollow organs with a predetermined diameter one pulls collagen material of adequate shape, after the reduction and after a first short heat treatment, onto a rod-like, solid body with smooth surface exhibiting the desired diameter and continues to treat for some minutes with steam-saturated hot air of about 1.5 atü at 80° to 100° C.

A silicon coated or covered glass-rod is preferably used as rod-like body.

In order to obtain a collagen preparation in the form of a bag-like hollow organ with a predetermined diameter one pulls the pericardium of a bovine, after the reduction treatment and a first short hot treatment, onto a silicon coated glass flask, continues with the hot treatment, removes the shaped bag and sterilizes in a common way.

In order to obtain a collagen preparation in form of a wadding-like or wool-like material one starts out from a rasped corium material or interstitial mammalian tissue.

An object of the invention is also to provide a process for producing the collagen I preparations described above, the process comprising the process features mentioned above and being listed for the characterization of the preparations.

A further object of the invention is the use of the preparations mentioned above for the human and veterinary therapy for the surgical care of defective body surfaces, as implants and transplants in order to replace skin, ligaments, tendines, tendon sheaths, hollow organs, vessels and the female breast.

As starting materials for the preparations of the invention collagen-I-material, preferably from goats, especially from bovine and fetusses from bovine is used which consists at least out of 90% collagen of type I and which is for instance the skin, the corium, tendines, ligaments, blood vessels, the pericardium and the interstitial mammalian tissue of the mammals mentioned. The type of the starting material depends thereby especially on the desired use in the human or veterinary science.

For the care of body surface-(skin)-defects (heterologous skin graft, wound plaster, swabs) for instance after burnings and other accidental injuries hides with their biological texture are used.

In order to support the osteoneogeneses after fractures, with or without the loss of substance, fascie of different strength and mainly the corium, especially from adult bovine without epidermis, are used as such or as being cleaved into thin layers.

Cord-like formations out of tendines, such as for instance bending tendines of bovine, are used as preparations for the replacement of ligaments (heterologous ligament replacements in connection with ruptures of tissue ligaments). For the production of elastic tubes for defective tubular hollow organs (blood vessels, bile duct, and so on), preferably duct-like formations out of tubular hollow organs, such as collagen tubes obtained from arteries, and fascie being sutured to give a tube are used. For the replacement of tendon sheaths practically all collagen formations such as those mentioned above can be used.

For the production of bag-like structures, for instance replacement preparations for the breast, one starts ou from the pericardium of bovine. In order to obtain wadding- or wool-like filling material one starts out from rasped material, especially rasped corium material or from interstitial mammalian tissue.

Thick collagen systems, for instance such as the cord-like formations out of tendines, are preferably subjected to a proteolysis before the real process and are then given the desired thickness by being cleaved in longitudinal direction parallel to the direction of the fibers. Therefore for instance the usable part of the bending tendine of bovine having a length of 30 to 40 cm and being as strong as the middle finger is preferably subjected as such to a proteolysis of 24 hour. The desired band strength (for instance with a strength of about 2.5 mm and more) is then obtained by cleaving it in longitudinal direction parallel to the direction of the fibers. Then a subsequent proteolysis of 24 hours follows. Preferably a knot is then made into one end of the band and then subjected to the further process steps.

In case hairy hides are used as starting material, a depilation is performed before the real process whereby one proceeds according to the "liming" known from the tanning technique. In order to do so the hides are preferably put into slaked lime to which 1 g of sodium sulfite has been added per kg. After about 6 to 10 days the hides are washed with water, then put for 3 hours into acetic acid (1%) and then washed with water once more for 24 hours.

Suitably the starting material should be isolated directly after killing (slaughtering) the animals. If the process for preparing the preparations according to the invention is not immediately following, the collagen systems can be conserved almost unlimitedly by freezing and storing at deep freezer temperatures. Such conservation is also possible after depilation.

The process according to the invention is equally suited for all mentioned starting materials. However, it may be suitable to use different reaction times, reaction temperatures and/or concentrations in one or more process steps depending on the type of the used starting material. Percentages stated herein are always weight percentages.

The proteolysis is performed especially with the protease used in the leather industry for the switch and the mordant and at the reaction conditions suitable therefore. It has been found especially suitable to perform the proteolysis in the presence of ficin and L-cysteine whereby one uses preferably an aqueous solution at a pH-value of about 5.5 to about 6.5 and especially 6, and at a temperature of 30° to 50° C., especially at about 37° C. The adjustment of the pH-value is performed adequately by adding 1N trisodiumcitrate buffer. The reaction time is normally 8 to 24 hours depending on the thickness of the collagen system.

In order to cross-link the peptide structure of the collagen-I preparation one uses di- or poly-functional aldehydes such as for instance alkane dialdehydes with 2 to 10 and especially 4 to 7 carbon atoms, but also formaldehyde (dihydroxymethylene). Glutaric dialdehyde has been found especially suitable due to its high penetration capacity and the great diffusion potential. The modification of the degree of the cross-linkage of the collagen and therefore the stiffness of the material depends strongly on the concentration of the cross-linking agent. Especially the production of material for hollow organs (blood vessels, etc.) requires a specifically soft and flexible material. The concentration (values given refer to glutaric dialdehyde) are generally between 1 and 10% by weight, whereby the preferred concentrations for hides with biological texture, fascie and corium are 3 to 5%, for cord-like formations out of tendines are 5 to 10%, for duct-like formations out of tubular hollow organs are 1 to 3% and for the production of a heterologous replacement of tendon sheaths are about 5 to 8%. In general the material is placed in an aqueous solution of the aldehyde and stays there for some days, adequately for about 7 days, at room temperature.

The reduction is perferably performed with a reducing bleaching agent used in the leather industry under the conditions suitable therefore, especially, however, with an alkali borohydride such as for instance sodium borohydride. By this reduction the insolubility of the collagen in an acidic and alkaline medium is achieved and at the same time the stiffness of the material caused by the cross-linking process is almost compensated. The material becomes more flexible. It maintains, however, its tear resistance. The additional bleaching effect caused thereby is very advantageous especially for the use as wound plaster. The reduction with the alkali metal borohydride is performed in an aqueous medium. It is in general possible to use as much sodium borohydride as is necessary in order to obtain an evenly white bleached surface. In general one uses 0.5 to 1.5 g of sodium borohydride/liter of water. For the reduction the material is placed in the aqueous sodium borohydride solution and stays therein for some hours, generally 4 to 24 hours.

The sterilization can be performed according to the commonly used method for the sterilization of a surgical material. A sterilization with an aqueous alcohol in the presence of low amounts of propylene oxide, such as for instance placing the material in 50% aqueous ethanol containing 1% by weight propylene oxide during about 10 days has been found very suitable, especially for a subsequent storage ready for use. The material sterilized according to this method is then placed into a sterile, buffered sodium chloride solution (BSS) from which the remaining sterilizing solution is evaporated, for instance in a thermostat within 3 to 8 hours.

This type of material is ready for use and can be stored. In order to prevent a deposition of calcium salts the sodium chloride solution should be free from calcium ions. In case a storage in a sterile vacuum packing (that means in dry form) or in a native collagen solution is preferred with respect to the future use the sterilization can be followed by a lyophilization (freeze-drying) or by a drying in the air. Especially for the preparations for skin substitutes a storage in a native callagen solution is suitable since the solution itself influences the healing process positively.

In order to prevent that, despite the washing with water, the proteolysis continues slightly due to not completely removed protease remainders, it is very suitable to perform an additional treatment with sodium chlorite ($NaClO_2$) after the process step of the proteolysis whereby the proteolysis is stopped. Preferably a diluted aqueous sodium chlorite solution, for instance a 1% solution, is used.

In order to increase the elasticity the collagen material obtained after the reduction step can be subjected to heat treatment with steam saturated air before the sterilization. This is performed in general for some minutes at a temperature of 80° to 100° C. (maximum) and at a pressure of 1.5 bar. The heat treatment can be performed in a common steam sterilization vessel.

In order to obtain smooth, sealed surfaces, the collagen material can be, during the second part of the heat treatment, brought into contact with the surface of an inert, smooth solid body being inert with respect to the material, such as for instance glass, which has been heated to about 80° to 100° C. (maximum). Silicone covered surfaces are also suitable for these purposes. This hot contact treatment lasts generally some minutes, for instances 1 to 15 minutes.

The hot contact treamtment is especially important for the sealing of the inner surfaces of hollow organs, such as for instance of blood vessels, since completely sealed and smooth inner surfaces can be obtained by this method in contrast to the modified blood vessels ("bovine heterograft") of the prior art used up to now.

According to the present process vessels with a predetermined diameter can be rather easily produced by pulling the collagen material (for instance tubes obtained from arteries or fasciae preparations sutured to give tubes) onto a rod-like support, for instance a silicone covered glass rod of predetermined strength and then subjecting it to the hot treatment. Thereby the starting material on the glass rod shrinks and assumes in its entire length a uniform, predetermined diameter. In this manner the diameters of vessels can be adjusted by suitable selection of the diameter of the support material. It is furthermore possible to achieve the elasticity of rubber tubes being absolutely sealed.

In a similar manner also pieces of said material can be made impervious by the hot treatment without being sutured or without any mechanical aid whereby the joints fuse together. This is especially important for the connection of pieces of vessels, since the natural sources, i.e. the isolated pieces, exhibit only a limited length and since longer pieces have been obtained up to now only by suturing together shorter pieces. The suturing process can be replaced by the "welding" process, what bears the especial advantage that there are no linkages at the fusing spots.

The collagen preparations obtained by the process of the invention are very well suited for surgical care of defective body surfaces, fractures, ruptures, defective tendon sheaths and defective hollow organs. Object of the invention is therefore also the use of the collagen preparations obtained according to the process of the invention.

The preparations produced according to the invention are not only tolerated by the recipient but also integrated. Covers of body surfaces are integrated for a short time and cast off after granulation has taken place. It has been found that the collagen type obtained from bovine and goats is harmless for the human being since its sequence of amino acids corresponds almost to that one of the human collagen.

EXAMPLE 1

The hide of a bovine or a goat is—as usual in tanning—depilated, by soaking it in slaked lime, which contains 1 g of sodium sulfite per kg of slaked lime. After 6 to 10 days the hide is watered, then soaked in 1% acidic acid for 3 hours and then again washed with water for 24 hours. The so obtained hide is depilated.

From this hide a piece of $40 \times 40$ cm is cut out and soaked in 3 liters of proteolysis solution which was adjusted to pH 6 with 1N trisodium citrate buffer. Said proteolysis solution contains 30 g of ficin and 3 g of L-cysteine in water. The proteolysis solution is allowed to react with this piece of hide for about 16 hours at 37° C. It is subsequently washed with water for 24 hours under running water. Then the piece of hide is soaked in 1% sodium chlorite solution ($NaClO_2$), then again 24 hours in running water. Afterwards the piece of hide is soaked for 7 days in an aqueous 3% glutaric dialdehyde solution in which it is moved from time to time and again soaked for 24 hours in running water. The preparation is transferred into an aqueous 1% sodium borohydride ($NaBH_4$) solution, again watered for 24 hours, sterilized for 10 days at room temperature in an aqueous 50% ethyl alcohol solution containing 1% propylene oxide and soaked in a sterile buffered sodium chloride solution. The solution is heated in a thermostat to 60° to 90° C. to evaporate the remaining sterilization solution for 3 to 8 hours. The so obtained finished preparation can be stored either in native collagen solution or after lyophilisation in sterile vacuum packing.

EXAMPLE 2

8 flexor tendines of bovine (30 to 40 cm in length, with a diameter of 2 to 2.5 cm) are soaked for 24 hours at pH 6 and 37° C. in 3 liters of the proteolysis solution described in example 1. Then the tendines are cleaved parallel to the fibers to give tapes of about 2 to 3 mm thickness. The so obtained are again soaked for 24 hours at 37° C. and pH 6 in 3 liters of the proteolysis solution described in example 1. The tapes are washed with water and treated with sodium chlorite solution as described in example 1 and are cross-linked with a 4% aqueous glutaric dialdehyde solution. Further treatment and sterilization is carried out as described in example 1.

EXAMPLE 3

Bovine hide is depilated as described in example 1. Then the epidermis is removed in a known manner to obtain the corium. A piece of corium of about 40×40 cm is frozen and subsequently rasped. The rasped material is proteolyzed in 3 liters of proteolysis solution as described in example 1, also further treatment is carried out as described in example 1 to yield a fibrous woolly material.

EXAMPLE 4

From the udder of a freshly slaughtered cow 800 g of interstitial mamma tissue are isolated and according to example 1 proteolyzed and further treated according to example 1. Similar to example 3 a fibrous woolly filling material is obtained.

EXAMPLE 5

8 to 10 pieces of body arteries of 30 to 50 cm in length and 1 to 2.5 cm in diameter, isolated from freshly slaughtered bovine, are soaked in 3 liters of proteolysis solution as described in example 1. These preparations are further treated according to example 1. However, a 1 to 2% aqueous glutaric dialdehyde solution is used for cross-linking allowing to react the solution for about 12 to 16 hours. The further steps up to the reduction inclusively were carried out according to example 1. The so obtained preparations are then hot treated in a common steam sterilization vessel with steam saturated air at about 80° to 100° C. maximum and at a pressure of about 1.5 bar. The time of treatment is 2 to 8 minutes. After the hot treatment the artery pieces are pulled on to one or more glass rods which are coated with a thin silicone film. Several artery pieces can be applied on one glass rod one behind the other, so that the edges of the artery pieces are closely adjacent. The whole arrangement is then hot treated for 2 to 10 minutes in a steam sterilizer as described above. As a result the adjacent edges of the artery pieces "fuse together" and all artery pieces assume the inside diameter defined by the glass rod. After some minutes the preparation is removed from the sterilizer and the glass rod is pulled out of the preparation. The so obtained collagen tube has a constant inside diameter and a completely smooth and sealed inner surface. Sterilization and storage can be carried out in the same way as described in example 1.

EXAMPLE 6

The pericardium of a freshly slaughtered goat is subjected to proteolysis treatment and to the further process steps described in example 1 up to the washing following the reduction step, inclusively. However, a 1% glutaric dialdehyde solution is used for cross-linking wich is allowed to react for about 12 to 16 hours. After reduction and washing the pericardium is hot treated as described in the preceding example in a steam sterilizer at 90° C. and at about 1.5 bar for about 5 minutes. Then the pericardium removed from hot treatment is pulled over the convex phase of a glass bowl having the shape of a female breast and being coated with a siliconfilm, the whole is again placed into the steam sterilizer for 5 to 10 minutes. The preparation is removed from the sterilizer, allowed to cool, pulled off the glass bowl and sterilized as described in example 1.

EXAMPLES OF APPLICATION (A) A collagen preparation prepared according to example 6 shaped as a female breast is implanted and filled with a filling material prepared according to example 3 or 4 and serves as breast substitute in plastic surgery. The filling material prepared according to example 3 or 4 can also be used in plastic surgery for breast enlargement. This material possesses distinct advantages compared to silicone materials used until now for this purpose. The filling material of the invention does not migrate but is gradually and completely integrated into the natural breast tissue.

(B) From a corium preparation obtained by the removal of the epidermis of a hide preparation according to example 1 adhesive plasters, swabs and tampons are cut. After lyophilisation they are sterile and dry packaged. They can then be used at any time as plasters, swabs and tampons which can also remain in the wound.

(C) A preparation prepared according to example 1 is adjusted on the operating table to the necessary form and size with scissors prior to use. The flat preparation is laid on the wound, sutured with continuous suture, the edges not overlapping. The stitches are taken out after 14 days. Casting off of the implant begins with lifting of the edges after 18 to 20 days and is finished after about 3 to 7 weeks.

(D) In case of a tendon rupture a tubular preparation prepared according to example 5 is pulled over the tendon stump prior to suturing the tendine and is finally positioned after suturing the tendine. Prior to administration the tubular preparation can also be cleaved in longitudinal direction, in order to cover the tendine and to suture then with everted suture. By this way an excellent tendon sheath substitute is obtained which is integrated into the body tissue.

What is claimed is:

1. A collagen preparation comprising collagen-I for human or veterinary therapy obtained by the following consecutive steps:
    (a) proteolyzing mammalian collagen-I material in presence of ficin and L-cysteine in an aqueous medium at a pH value of 5.5–6.5 and at a temperature of 30° to 50° C.,
    (b) cross-linking the material obtained according to step (a) with at least one aliphatic dialdehyde of 2 to 10 carbon atoms,
    (c) reducing the material obtained according to step (b) with a reducing bleaching agent and
    (d) finally sterilizing the material, wherein the texture of the collagen-I material is preserved throughout all steps.

2. A collagen preparation according to claim 1, wherein skin, corium, fasciae, tendons, blood vessels, tubular hollow organs, pericardia, and interstitial mammal tissue is the mammalian collagen-I material.

3. A collagen preparation according to claim 1 wherein the collagen-I material is derived from goats, bovine, and bovine fetuses.

4. A collagen preparation according to claim 1 wherein the aliphatic dialdehyde has 4 to 7 carbon atoms; the reducing is effected with an alkali metal borohydride in an aqueous medium; and treated for some minutes at 80° to 100° C. with hot air saturated with steam to mold the same and, finally sterilizing the so obtained collagen-I material.

5. The collagen preparation of claim 1 wherein after a collagen material is subjected to the first proteolysis of Step A the desired thickness is achieved by cleaving said collagen parallel to the direction of the fibers, proteolyzing again and continuing the treatment in the remaining steps according to claim 1.

6. A collagen preparation of claim 1 or 5 where there is a treatment with dilute aqueous sodium chlorite solution after the proteolysis.

7. A collagen preparation of claim 1, 4 or 5 including washing with running water between the individual process steps.

8. A collagen preparation of claim 1 obtained by treating mammalian collagen-I with an aqueous solution containing 10 g ficin per liter and 1 g L-cysteine per liter at a pH value of about 6 and at a temperature of about 37° C. for 8 to 24 hours, then sequentially treating with a 1% by weight aqueous sodium chlorite solution for 24 hours, washing with water, treating with a 1 to 10% by weight aqueous glutaric dialdehyde solution for 7 days, washing with water, treating with an aqueous sodium borohydride solution for 24 hours, washing with water and then sterilizing, wherein the washing is performed with running water for 24 hours, respectively.

9. The collagen preparation of claim 1 formed in the shape of a hollow tube having a defined diameter by coating a smooth surfaced solid bar with said collagen material, and after treating said collagen according to steps (a) to (c) of claim 1, additionally treating with hot air saturated with steam at 80° to 150° C. and about 1.5 bar and sterilizing it.

10. A collagen preparation according to claim 9 wherein said bar is a glass rod coated with silicone.

11. A collagen preparation of claim 1 in the shape of a bag like hollow organ having a defined diameter obtained by applying a bovine pericardium to a silicone coated glass flask of a desired diameter and after the reducing step, the shaped pericardium is heated and sterilized.

12. A collagen preparation of claim 1 starting from rasped corium material or interstitial mammalian tissue to obtain a cotton like or woolly filling material.

13. A collagen preparation according to claims 1, 4, 5, 8, 9, 11 or 12, which is sterilized by treating the finished collagen preparation for some days with about 50% by weight of aqueous ethyl alcohol, containing about 1% by weight propyleneoxide, then tansferring the preparation into a sterile buffered sodium chloride solution and heating the sodium chloride solution to evaporate the remaining sterilization solution during several hours.

14. The collagen of claim 1 prepared by the consecutive steps of:
(a) proteolyzing mammalian collagen-I material,
(b) cross-linking the material obtained according to step (a),
(c) reducing the material obtained according to step (b) and
(d) finally sterilizing the material,
wherein, the material obtained according to step (c) is heated, molded and "welded" where pieces of said material are to be connected and wherein the texture of the collagen-I material is preserved throughout all steps.

15. The preparation of claim 4 wherein the cross-linking is effected with a 1 to 10% by weight of aqueous glutaric dialdehyde solution.

16. A method of surgical repair of defective parts of the body of a mammal comprising replacing the defective parts selected from the group consisting of skin, ligaments, tendons, tendon sheaths, hollow organs, blood vessels and mama with a collagen preparation of claim 1.

17. The preparation of claim 1 wherein the material obtained by step (c) is heated to mold the same.

18. A collagen-I preparation of claim 1 wherein the material obtained by step (c) is heated to mold and weld pieces of said material to connect them.

19. A process for preparation of a collagen-I preparation comprising
(a) proteolyzing mammalian collagen-I material in presence of ficin and L-cysteine in an aqueous medium at a pH value of 5.5–6.5 and at a temperature of 30° to 50° C.,
(b) cross-linking the material obtained according to step (a) with at least one aliphatic dialdehyde of 2 to 10 carbon atoms,
(c) reducing the material obtained according to step (b) with a reducing bleaching agent and
(d) finally sterilizing the material,
wherein the texture of the collagent-I material is preserved throughout all steps.

20. A collagen-I method of claim 19 wherein the material obtained by step (c) is heated to mold and weld pieces of said material to connect them.

21. A collagen-I method of claim 19 wherein the material obtained by step (c) is heated to mold the same.

* * * * *